(12) United States Patent
Tien

(10) Patent No.: US 7,415,302 B2
(45) Date of Patent: Aug. 19, 2008

(54) METHOD AND SYSTEM FOR LEADING MACROMOLECULE SUBSTANCES INTO LIVING TARGET CELLS

(76) Inventor: Der-Yang Tien, 19F., No. 70, Sec. 2, Dunhua S. Rd., Da-An District, Taipei (TW)

(*) Notice: Subject to any disclaimer, the term of this patent is extended or adjusted under 35 U.S.C. 154(b) by 640 days.

(21) Appl. No.: 10/767,387

(22) Filed: Jan. 28, 2004

(65) Prior Publication Data
US 2005/0085711 A1    Apr. 21, 2005

(30) Foreign Application Priority Data
Oct. 15, 2003    (TW) .............................. 92128522 A

(51) Int. Cl.
*A61B 5/05*    (2006.01)
(52) U.S. Cl. .................... 600/427; 600/439; 604/20; 604/21
(58) Field of Classification Search ......... 600/407–483; 604/19, 20, 606
See application file for complete search history.

(56) References Cited

U.S. PATENT DOCUMENTS

| | | | |
|---|---|---|---|
| 6,298,264 B1 * | 10/2001 | Zhong et al. | 604/20 |
| 6,306,403 B1 * | 10/2001 | Donovan | 424/239.1 |
| 6,654,636 B1 * | 11/2003 | Dev et al. | 604/21 |
| 2003/0028111 A1 * | 2/2003 | Vaezy et al. | 600/439 |
| 2005/0038340 A1 * | 2/2005 | Vaezy et al. | 600/439 |
| 2006/0069166 A1 * | 3/2006 | Vargas et al. | 514/738 |

* cited by examiner

*Primary Examiner*—Brian L. Casler
*Assistant Examiner*—Nasir Shahrestani
(74) *Attorney, Agent, or Firm*—Sawyer Law Group, LLP

(57) ABSTRACT

A method and system for leading macromolecule substances into target cells includes an image picking unit, an image merging unit, an injection unit, and an energy conversion module. The image picking unit is used for picking up the three-dimensional (3D) and the 3D blood vessel photographic images of the tissue or organ where the target cells locate. The image merging unit is used for merging the 3D structure images into the 3D blood vessel photographic images, therefore choosing a blood vessel passage fully covering the target cells for transmitting the macromolecule substances. The injection unit is used for injecting liquid and transmitting the macromolecule substances to the target cells. The energy conversion module is used for exerting energy to activate the liquid to perform biological effects, thereby forming non-permanent holes in the cell membranes of the target cells. The macromolecule substances enter into the target cells through the non-permanent holes.

4 Claims, 2 Drawing Sheets

METHOD AND SYSTEM FOR LEADING MACROMOLECULE SUBSTANCES INTO LIVING TARGET CELLS

FIELD OF THE INVENTION

The present invention relates generally to a method and system for leading macromolecule substances into living target cells, and more particularly, to a method and system which applies ultrasonic wave to adjust the permeability of cell membranes of the target cells, thereby efficiently leading low dosage macromolecule substances into the target cells.

BACKGROUND OF THE INVENTION

Tissue cells of a human body are sometimes stimulated by inner or outer harmful factors which make them ill. As a result, the number of ill cells increases rapidly, and the ill cells transfer to healthy tissues. Thus a tumor is formed. Tumors include benign tumors and malignant tumors. Compared with benign tumors, malignant tumors are hard to cure, and do a greater harm to human bodies.

At the present time, 5,000,000 people die every year because of tumors, and malignant tumors are the main killer. With the development of medical sciences, a lot of advanced tumor diagnostic methods and treatment methods are provided. Tumor treatment methods mainly include surgery, chemotherapy and actinotheraphy. In a chemotherapy treatment, health of a tumor patient is generally threatened by yet-to-solved limitations and drawbacks of low medication precision, which distributes toxicity of medicines to the human bodies. Therefore, how to achieve a maximum curative effect with a minimum medicine dosage, and how to improve the medication precision are the problems people eager to overcome.

Recent research discovers that energy generated by shock wave lithotripsy (SWL) can produce tiny bubbles around cells. These tiny bubbles form non-permanent holes in the cell membranes. Thus, the permeability of the cell membranes is improved, and better medicine absorbency is achieved. U.S. Pat. No. 6,298,264 discloses a method for improving the permeability of cell membranes. The method applies a first pulsed wave (PW) and a second PW to produce tiny bubbles around cells. These tiny bubbles form non-permanent holes in the cell membrane to improve the permeability of the cell membranes. The method increases the permeability of cell membrane to 90%. Therefore a low medicine dosage is needed. However, the method does not disclose how to precisely locate the target cells and how to improve the medication precision. Thus, a method for precisely locating target cells and improving medication precision is desired.

SUMMARY OF THE INVENTION

The primary objective of the present invention is to provide a method and system for efficiently leading macromolecule substances into target cells.

Another objective of the present invention is to provide a method and system applied in gene delivery, which increases the efficiency of gene delivery.

A further objective of the present invention is to provide a method and system applied in gene therapy, which improves the efficiency of gene therapy.

And yet another objective of the present invention is to provide a method and system for improving medication precision.

Still another objective of the present invention is to provide a method and system for lowering medicine dosage and efficiently leading the medicine into tumor cells.

In accordance with the above and other objectives, the present invention proposes a method and system for leading macromolecule substances into living target cells. The system for leading macromolecule substances into living target cells comprises: an image picking unit, the image picking unit used for picking up the three-dimensional (3D) structure images of the tissue or organ where the target cells locate, and the 3D blood vessel photographic images of the tissue or organ where the target cells locate; an image merging unit, the image merging unit used for merging the 3D structure images into the 3D blood vessel photographic images, therefore choosing a blood vessel passage fully covering the target cells for transmitting the macromolecule substances; an injection unit, the injection unit used for injecting liquid and transmitting the macromolecule substances to the target cells; an energy conversion module, the energy conversion module used for exerting energy to activate the liquid to perform biological effects, thereby forming non-permanent holes in the cell membranes of the target cells; wherein the macromolecule substances enter into the target cells through the non-permanent holes in the cell membranes thereof.

The method for leading macromolecule substances into living target cells comprises: firstly, picking up 3D structure images of the tissue or organ where the target cells locate, and 3D blood vessel photographic images of the tissue or organ where the target cells locate; secondly, merging the 3D structure images into the 3D blood vessel photographic images, choosing a blood vessel passage fully covering the target cells for transmitting the macromolecule substances; thirdly, injecting tiny bubbles liquid (ultrasonic wave or synthetic blood) by using a pipe along the chosen blood vessel passage, the tiny bubbles being arranged around the target cells; fourthly, exerting energy to activate the tiny bubbles liquid to perform biological effects, thereby forming non-permanent holes in the cell membranes of the target cells; and finally, injecting the macromolecule substances into the target cells through the non-permanent holes in cell membranes along the chosen blood vessel passage.

Compared with conventional medication method and system, the method and system for leading macromolecule substances into living target cells of present invention picks up the 3D structure images of the tissue or organ where the target cells locate, and the 3D blood vessel photographic images of the tissue or organ where the target cells locate, merges the 3D structure images into the 3D blood vessel photographic images, thereby precisely locating the target cells for choosing a most efficient blood vessel passage fully covering the target cells, and injects the macromolecule substances into the target cells along the chosen blood vessel passage. Then, the method and system exerts energy to activate tiny bubbles liquid arranged around the target cells to perform biological effects, thereby forming non-permanent holes in the cell membranes of the target cells. The macromolecule substances enter into the target cells through the non-permanent holes in the cell membranes thereof. Thus the method and system for leading macromolecule substances into living target cells of present invention has many advantages, such as low medicine dosage, low cost, precisely medication, and efficient curative effect.

To provide a further understanding of the invention, the following detailed description illustrates embodiments and examples of the invention, it is to be understood that this detailed description is being provided only for illustration of the invention and not as limiting the scope of this invention.

DETAILED DESCRIPTION

The present invention relates generally to a method and system for leading macromolecule substances into living target cells, and more particularly, to a method and system which applies ultrasonic wave to adjust the permeability of cell membranes of the target cells, thereby efficiently leading low dosage macromolecule substances into the target cells. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

A method and system for leading macromolecule substances into living target cells of the present invention can be applied to a variety of different fields, such as gene delivery, gene therapy, medicine transmission, partial medication and tumor treatment. The present invention is particularly suitable for tumor treatment, and more particularly, for solid tumor treatment. In a solid tumor treatment, for example, a preparatory step is usually taken by computed tomography (CT) or magnetic resonance imaging (MRI). Three-dimensional (3D) structure images of the tissue or organ where tumor cells locate are picked up by the preparatory step, as a basis for subsequent treatments (such as surgery, chemotherapy and actinotheraphy).

Figure 1:
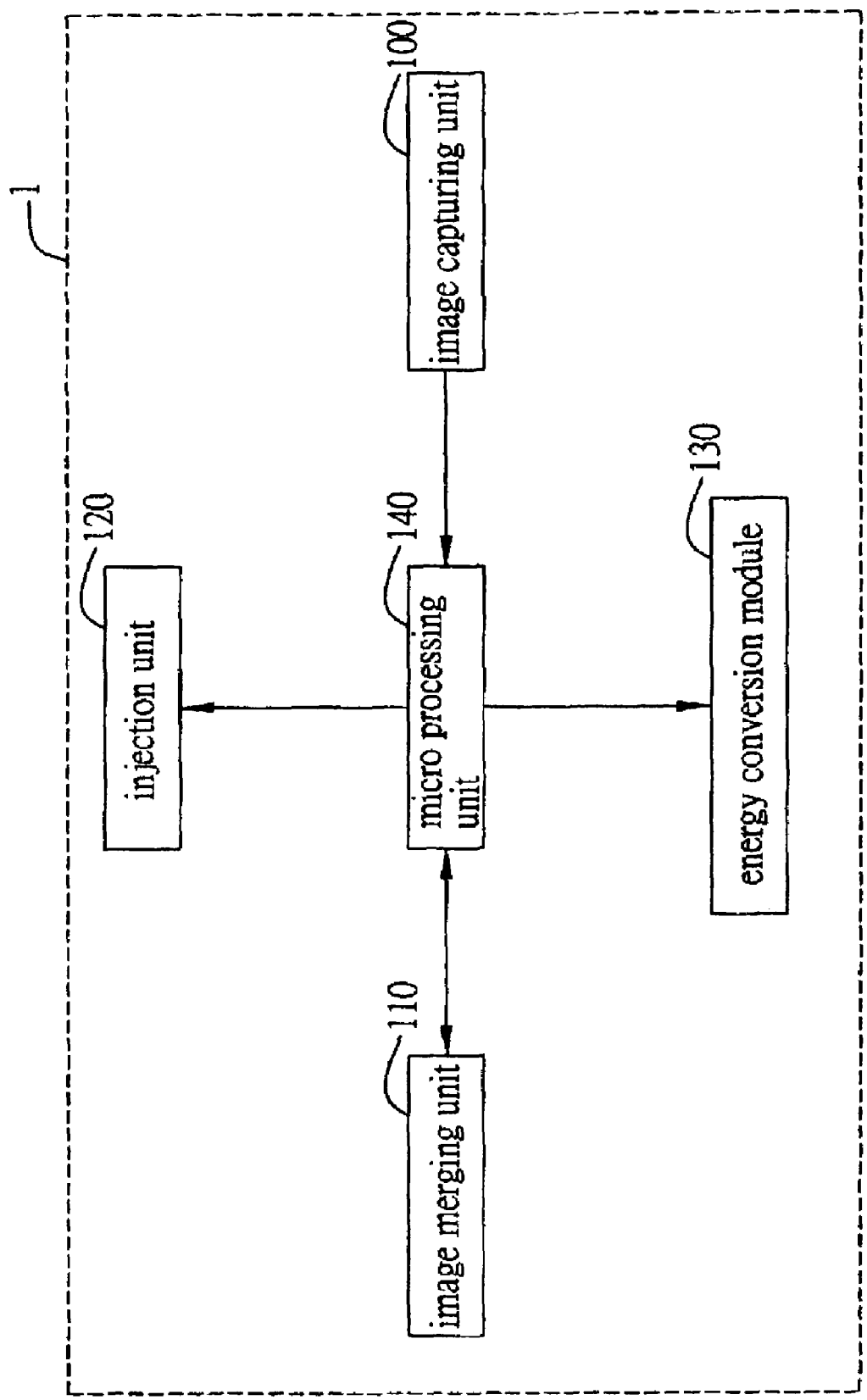
FIG. 1 is a block schematic diagram illustrating a basic structure of a system for leading macromolecule substances into living target cells in accordance with the preferred embodiment of the present invention
Figure 2:
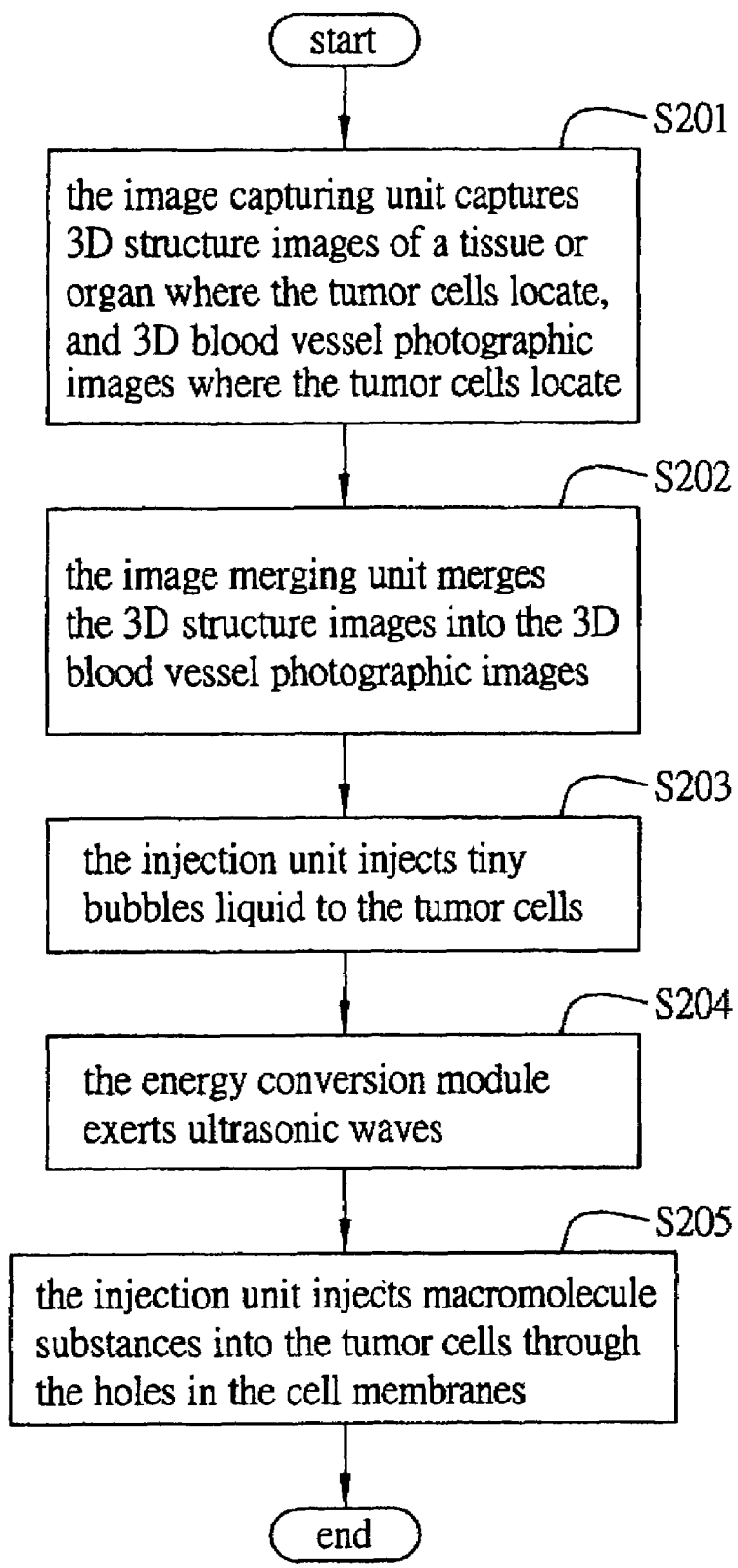
FIG. 2 is a flow chart illustrating steps for leading macromolecule substances into living target cells by using the system of FIG. 1.

Referring to FIG. 1, a basic structure of a system for leading macromolecule substances into living target cells in accordance with the preferred embodiment of the present invention is illustrated. FIG. 1, including FIG. 2, is only for concisely illustrating the essential elements of the system 1 for leading macromolecule substances into living target cells. A practical used system 1 can be more complicated.

The system 1 for leading macromolecule substances into living target cells comprises an image picking unit 100, an image merging unit 110, an injection unit 120 and an energy conversion module 130. In present embodiment, the image picking unit 100, image merging unit 110, injection unit 120 and energy conversion module 130 is controlled by a micro processing unit 140.

The image picking unit 100 is applied for picking up 3D structure images of the tissue or organ where the target cells locate, and for picking up 3D photographic images of the blood vessel where the target cells locate. In present embodiment, the image picking unit 100 is one of the CT device, MRI device and blood vessel photographic device. The target cell is at least one tumor cell.

The CT device applies fan-shaped X-ray to scan a layer of a human body, generally in axial direction, and applies a row of detectors to receive signals penetrated through the human body. The detectors receive signals from a specific layer and in a specific direction when an X-ray emitter is fixed in a corresponding specific place. When the X-ray emitter is rotated around a layer, the detectors located opposite the X-ray emitter receive signals from the same layer, but in different directions. Computer analyzes the signals and calculates out the density distribution of the composed dots of the layer, then displays the image with dot patterns of different gray level, for enhancing the resolution of the layer. To scan a brain, about fifteen pieces of 1 centimeter thick layer can fully cover the whole cerebrum and cerebellum, and the tiny structure of the brain can be displayed. Thus hydrocephalus or blood gore is whether or not in the brain can be detected. Presently, a quick whole-body type scanner can scan a liver in thirty seconds under the circumstance of a patient holding his/her breadth for greatly reducing the interference of breadth and intestine moving. Other diseases, such as small liver cancer, adrenal tumor or pancreatic diseases can be quickly detected and clearly displayed by using the scanner.

The MRI device is used for providing clear multilayer photography. The MRI device applies electromagnetic waves to stimulate a patient, and applies detectors to receive the echoes released from the patient. After many times of complicated stimulate-echoes processes, high resolution image can be achieved according to the enormous echoes data. Different tissue releases different echoes after being stimulated, thereby producing distinct comparison among the images obtained. Compared with the CT device, which generally scans layers in axial direction (at most plus a coronal plane in the brain), the MRI device can scan a portion of a human body from different angles, such as a special portion like hypophysis or brainstem, whose structure can be clearly displayed. Another aspect, the MRI device does not apply X-ray, and the scan inspection can be finished in fifteen minutes, thus radiation to the human body is greatly reduced. Furthermore, in a nerve system, many diseases, like slight apoplexy of brainstem, small tumor adjacent the bottom of a skull, or spinal cord disease (such as acute trauma of spinal cord or lumbar disc herniation (LDH)), can be easily detected by the MRI device, but usually be ignored by the CT device. In a skeleton and muscular system, the MRI device is particularly suitable for checking diseases affecting the arthrosis and parenchyma, such as sport injuries. The MRI device can also be used to check bile duct. In a bile duct inspection by using the MRI device, the images of the bile duct can be obtained in twenty seconds under circumstance of a patient holding his/her breadth, thereby the suffering of endoscopic retrograde cholangio pancreatography (ERCP) can be avoided.

Although the MRI device has many advantages as mentioned above, the costs for checking are so high as to the MRI checking can not be widely used. Furthermore, if a patient girds a pacemaker or other patient monitors, the checking efficiency by using the MRI device is limited. Therefore, proper method for picking up 3D structure images of a tissue or organ should be selected according to the where the tumor locates and the personal situation of the patient. Although CT device and MRI device can efficiently pick up 3D structure images of a tissue or organ, medicine transmission passage is usually out of control in medication by using injection method. Whether or not the medicine injected by using a pipe is efficiently transmitted to all of the tumor cells is also unsure. Thus a poor curative effect is resulted. To overcome the problem, the image picking unit 100 of the system 1 for leading macromolecule substances into living target cells in accordance with the present invention further comprises blood vessel photographic device.

The blood vessel photographic device injects special developer into the blood vessel for generating a series of blood vessel image. For example, in checking a heart blood vessel system, femoral is firstly pierced from inguen, a pipe is then put in and conversely transmitted into particular blood vessel. The developer is then quickly injected into the blood vessel through the pipe, and consecutive snapshots are simultaneously taken. Thus the blood flow situation of the organ where the blood vessel flows into, such as brain, heart, liver or kidney, can be obtained. Further, the 3D blood vessel photographic images can be obtained by using 3D reconstructed blood vessel photography, for example, by using diagnostic and interventional angiography system (Advantx LCA+), cardiovascular and angiography imaging system (Advantx LCV+) and biplane neuroangiography system (Advantx LCN+) manufactured by General Electric (GE) company to pick up the 3D blood vessel photographic images of the tissue or organ where the tumor cells locate.

The image merging unit 110 merges the 3D structure image picked up by the images picking unit 100 into the 3D blood vessel photographic images, for precisely locating the tumor cells, and for choosing a proper blood vessel passage fully covering the tumor cells. As mentioned above, after the CT device and 3D blood vessel photographic device, and/or the MRI device and 3D blood vessel photographic device respectively picking up the 3D structure images of the tumor cells and 3D blood vessel photographic images, the image merging unit 110 performs image merging operation (also called tissue mapping). The merged images are use for precisely locating the tumor cells, and for choosing a most efficient blood vessel passage. Medicine is injected through a pipe along the chosen blood vessel passage, thereby ensuring the medicine be efficiently transmitted to the tumor cells, and a thorough treatment and a low recrudesce chance be achieved.

Additionally, after image merging, the relative position of the tumor and the blood vessel around the tumor is precisely showed. Aside from the tumor cells can be precisely located, a most efficient blood vessel passage is also can be chosen. Therefore medicine can be precisely transmitted to all of the tumor cells through a pipe along the most efficient blood vessel passage.

The injection unit 120 applies a pipe for injecting tiny bubbles liquid, and the macromolecule substances into the target cells. The macromolecule substances enter into the target cells through the non-permanent holes formed by the tiny bubbles in the cell membranes thereof. In present embodiment, the tiny bubbles liquid is injected and distributed around the tumor cells through a pipe of the injection unit 120 along a chosen blood vessel passage. The size of the bubble is preferred to be smaller than 10 micron, for smoothly passing through the blood vessel. The step of injecting medicine through a pipe can be processed before the forming of the non-permanent holes in the cell membrane, or alternatively after that. Because the medicine enters into the tumor cells through holes formed in the cell membrane, the medicine dosage can be reduce to 1% as normal dosage, and a more efficient curative effect is achieved, damages to other cells because of the toxicity of the medicine is avoided, and a great deal of costs is saved.

The energy conversion module 130 is used for exerting energy to activate the tiny bubbles liquid to perform biological effects, thereby forming non-permanent holes in the cell membranes of the target cells. In present embodiment, the energy conversion module 130 can be an ultrasonic wave conversion module. The ultrasonic wave conversion module exerts ultrasonic waves of 1 Mpa intensity, and forms non-permanent holes in the cell membrane for facilitating the medicine entering into the tumor cells.

Referring to FIG. 2, steps for leading macromolecule substances into living target cells using the above mentioned system 1 are illustrated.

In step S201, the image picking unit 100 picks up 3D structure images of the tissue or organ where the tumor cells locate, and 3D blood vessel photographic images where the tumor cells locate. Step S202 is then processed.

In step S202, the image merging unit 110 merges the 3D structure images into the 3D blood vessel photographic images for precisely locating the tumor cells and choosing a blood vessel passage fully covering the tumor cells. Step S203 is then processed.

In step S203, the injection unit 120 injects tiny bubbles liquid around the tumor cells through the chosen blood vessel passage. Step S203 is then processed.

In step S204, the energy conversion module 130 exerts ultrasonic waves for activating the tiny bubbles liquid to perform biological effects, thereby forming non-permanent holes in the cell membranes of the tumor cells. Step S205 is then processed.

In step S205, the injection unit 120 injects macromolecule substances into the tumor cells through the non-permanent holes in the cell membranes thereof.

In another embodiment of the present invention, synthetic blood is injected around the tumor cells as tiny bubbles liquid. The synthetic blood has a pretty small volume about 150 nanometer, so that capillary vessel would not be jammed, and the synthetic blood would not enter into the apertures between the blood vessels. Thus oxygen deficiency resulted from low blood flow when using a pipe is improved.

Ultrasonic wave developer can also be applied to pick up the 3D blood vessel photographic images. The ultrasonic wave developer is composed of tiny bubbles enwrapped in special protection housing. First generation of developer is made of bubbles enwrapping air therein, such as albunex (mallinckrodt) having an average volume of 4μ, and made of albumin vibrated by ultrasonic waves. Other ultrasonic wave developers include echovist, echogen, levovist, aerosomes and so on. New generation ultrasonic wave developer is made of gas which is hard to be dissolved in water, such as fluorocarbon or sulfur tetrafluoride. Phospholipids, albumin, polymer, surfactant or other substances are added in the gas. The new generation ultrasonic wave developer can prolong the life thereof in the blood, and strengthen the ultrasonic wave dispersion effect. The size of the ultrasonic wave developer is preferred to be no larger than 10 micron, so that the ultrasonic wave developer can smoothly pass through the micro blood vessels. The ultrasonic wave developer used in method and system of present invention can be injected either by mainline or using a pipe.

When exerted with ultrasonic waves of 1 Mpa intensity, the bubbles of the developer perform non-linear oscillation, and emit harmonic signals. Because the harmonic signals of the bubbles are greatly stronger than that of the tissue, the developer signals are strongly distinct from that of the tissues, so that the situation of the tissues, including the blood flow situation of the cardiac muscle and kidney, and blood vessel distribution of the tumor, can be clearly displayed. As is mentioned above, after the 3D structure images merged into the 3D blood vessel photographic images, a most efficient blood vessel passage is chosen. The medicine for tumor treatment is injected around the tumor cells through the chosen passage.

After the medicine injected around the tumor cells, ultrasonic waves of at least 1 Mpa intensity, or shock waves of proper intensity are exerted for activating the tiny bubbles or ultrasonic wave developer to perform strong bubble movements, thereby forming non-permanent holes in the cell membranes, thereby increasing the permeability of the cell membranes, sharply lowering medication dosage, and maintaining efficient curative effect. Alternatively, the medicine can also be injected before the forming of the non-permanent holes in the cell membranes of the tumor cells, thereby achieving a same effect of precisely medicating as mentioned above.

Additionally, the system 1 for leading macromolecule substances into living target cells of present invention further comprises or cooperates with a data processing electronic device, for processing the data generated during the course of the system 1 working. The data processing electronic device can be a personal computer (PC), notebook computer (NB), server, working station, personal digital assistant (PDA), Liquid Crystal Display (LCD) computer, or tablet PC and so on. The data processing electronic device comprises a display unit and an input unit. The display unit is used for displaying the images merging process performed by the image merging unit 110, the medicine injection process performed by the injection unit 120, and energy transmitting situation of the energy conversion module 130. The input unit is used for inputting commands and/or parameters of the system 1 for leading macromolecule substances into living target cells of present invention to the data processing electronic device.

It should be apparent to those skilled in the art that the above description is only illustrative of specific embodiment and example of the invention. The invention should therefore cover various modifications and variations made to the herein-described structure and operations of the invention, provided they fall within the scope of the invention as defined in the following appended claims.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for leading macromolecule substances into living target cells, comprising:
   picking up three-dimensional (3D) structure images of a tissue or organ where the target cells are located;
   picking up 3D blood vessel photographic images of the tissue or organ where the target cells are located;
   merging the 3D structure images into the 3D blood vessel photographic images, choosing a blood vessel passage fully covering the target cells for transmitting the macromolecule substances;
   injecting synthetic blood by using a pipe along the chosen blood vessel passage, exerting energy to form non-permanent holes in cell membranes of the target cells; wherein the synthetic blood forms tiny bubbles around the target cells, thereby increasing the permeability of the target cells, and wherein the synthetic blood has a small volume such that the chosen blood vessel passage is not jammed; and
   injecting the macromolecule substances into the target cells through the non-permanent holes in cell membranes along the chosen blood vessel passage.

2. The method as claimed in claim 1, wherein the energy exerted for forming non-permanent holes in cell membranes of the target cells is an ultrasonic wave having an intensity of at least 1 Mpa.

3. The method as claimed in claim 1, wherein the macromolecule substances are injected into the target cells by using a pipe.

4. The method as claimed in claim 2, wherein the step of the macromolecule substances being injected around the target cells by using a pipe is performed before the forming of the non-permanent holes in cell membranes of the target cells.

* * * * *